United States Patent
Bouška et al.

(10) Patent No.: US 11,945,537 B2
(45) Date of Patent: Apr. 2, 2024

(54) FIRST AID KIT FOR THE INSIDE OF BICYCLE HANDLEBARS

(71) Applicant: Aid-in s.r.o., Ceske Budejovice (CZ)

(72) Inventors: Petr Bouška, Hluboká nad Vltavou (CZ); Jakub Stedina, Prague (CZ)

(73) Assignee: Aid-in s.r.o., Ceske Budejovice (CZ)

( * ) Notice: Subject to any disclaimer, the term of this patent is extended or adjusted under 35 U.S.C. 154(b) by 0 days.

(21) Appl. No.: 17/780,968

(22) PCT Filed: Nov. 26, 2020

(86) PCT No.: PCT/CZ2020/050087
§ 371 (c)(1),
(2) Date: May 28, 2022

(87) PCT Pub. No.: WO2021/104546
PCT Pub. Date: Jun. 3, 2021

(65) Prior Publication Data
US 2023/0002001 A1    Jan. 5, 2023

(51) Int. Cl.
*B62K 21/12*    (2006.01)
*A61F 17/00*    (2006.01)
*B62K 19/30*    (2006.01)

(52) U.S. Cl.
CPC .............. *B62K 21/12* (2013.01); *A61F 17/00* (2013.01); *B62K 19/30* (2013.01)

(58) Field of Classification Search
None
See application file for complete search history.

(56) References Cited

U.S. PATENT DOCUMENTS

| | | | | |
|---|---|---|---|---|
| 5,950,498 A | * | 9/1999 | Gossett | B62K 21/12 74/551.8 |
| 6,564,982 B1 | * | 5/2003 | Woods | B62K 21/12 74/551.8 |
| 2011/0062051 A1 | | 3/2011 | Miller | |

FOREIGN PATENT DOCUMENTS

| | | |
|---|---|---|
| CN | 202345836 | 7/2012 |
| CN | 108248733 | 7/2018 |

(Continued)

OTHER PUBLICATIONS

European Patent Office, International Search Report dated Feb. 19, 2021 in International Application No. PCT/CZ2020/050087 filed on Nov. 26, 2020.

(Continued)

*Primary Examiner* — Vicky A Johnson
(74) *Attorney, Agent, or Firm* — Thedford I. Hitaffer; Hitaffer & Hltaffer, PLLC

(57) ABSTRACT

The subject of the invention is a first aid kit into bicycle handlebars that comprises a compression storage portion, wherein the compression storage portion defines a space adapted for storing objects and an elongated retraction element attached to one end of the compression storage portion, wherein the other end of the compression storage portion is provided with a plug. The plug can be used to fix the compression storage portion in the handlebars and to define a clearance between the first aid kit and the handlebars. The retraction element (e.g., a string or a cord) can be used for retracting the compression storage portion into the handlebars. Furthermore, the first aid kit can comprise a firm storage portion which can provide an additional storage space.

4 Claims, 4 Drawing Sheets

(56) References Cited

FOREIGN PATENT DOCUMENTS

| | | |
|---|---|---|
| DE | 90 14 691 U1 | 2/1991 |
| EP | 2 386 471 A2 | 11/2011 |
| TW | 489127 U * | 11/2014 |

OTHER PUBLICATIONS

European Patent Office, Written Opinion dated Feb. 19, 2021 in International Application No. PCT/CZ2020/050087 filed on Nov. 26, 2020.
Incog bike multi-tool stores in you bandlebars View Gallery—11 images, Jun. 5, 2012, XP055774666, URL:https://newatlas.com/incog-bike-tool-handlebars/22812/, retrieved on Feb. 10, 2021.

* cited by examiner

FIRST AID KIT FOR THE INSIDE OF BICYCLE HANDLEBARS

This application, filed under 35 USC 371, is a United States National Stage Application of International Application No. PCT/CZ2020/050087, filed Nov. 26, 2020, which claims priority to CZ Application No. PV 2019-729, filed on Nov. 28, 2019, the disclosures of which are incorporated herein by reference.

TECHNICAL FIELD

The present invention relates to a first aid kit for a bicycle adapted to be stored inside handlebars.

BACKGROUND OF THE INVENTION

In the current state of the art, first aid kits intended for being carried on a bicycle are known. These first aid kits usually include basic elements of the first aid kit such as bandages, patches, disinfectants, blister patches, and pain and/or allergy medications. However, these are usually first aid kits in the form of pockets or bags attachable to a seat, handlebars, or a frame, usually by means of hook and loop straps, or attachable to a bottle holder or a carrier.

A first aid kit placed in a bag attachable to the bicycle frame is disclosed, for example, in the document CN202345836. The document CN108248733 then discloses a pocket with a first aid kit attachable to the bicycle frame.

All of the above solutions take up space on the bicycle, which in turn cannot be used for carrying or placing other accessories and/or baggage. Furthermore, a major shortcoming of these known solutions is that most cyclists do not use these solutions, either because of their appearance, ergonomics, fear of damage or theft, etc. Therefore, cyclists usually do not carry any first aid kit, or they carry it only occasionally. These shortcomings can be overcome, for example, by placing the first aid kit inside the handlebars.

The document U.S. 5,950,498 A discloses a storage device into a handlebar. A firm cylindrical box inserted into an opening in the handlebar is described, and the document also discloses the possibility of storing the first aid kit in this box. However, the storage space provided in this solution is relatively small because the box can be placed only in the straight ends of the handlebars, which means that the bandages stored may not be sufficient even for relatively minor injuries.

Therefore, it would be desirable to come up with a solution that would allow the first aid kit to be placed on the bicycle such that it does not interfere with riding, does not prevent placement of a classic cycling bag on the frame or handlebars, and, simultaneously, such that it provides enough space to store the necessary parts of the first aid kit.

SUMMARY OF THE INVENTION

The above shortcomings are eliminated to a certain extent by a first aid kit into bicycle handlebars, which comprises a compression storage portion and a retraction element. The compression storage portion defines a space adapted for storing objects, for example, common parts of a first aid kit such as bandages or a patch. The retraction element is attached to one end of the compression storage portion. The other end of the compression storage portion is provided with a plug.

Preferably, the compression storage portion has an approximately cylindrical shape complementary to the cylindrical opening in the handlebars. The compression properties thereof can be provided by the material chosen, i.e. it can be made of a flexible material, e.g. a flexible polymer (elastomer) such as silicone, or it can be made of fabric, or fibres interwoven in any way, which do not have to be of a compression nature themselves, but they are tightened in the radial direction under the action of axial force, as a result of a suitable interweaving, and when the tension is released, they can even be unweaved. The compression properties of the storage portion can be provided by the material chosen, arrangement thereof as well as by the technological procedure, e.g., by extracting air from interior of the compression portion. Leather or conventional fabric can also be used, from natural fibres, e.g., cotton, or synthetic fibres, e.g. polyethylene, or a combination thereof, or a synthetic material allowing vacuum compression of the contents.

An advantage of the compression storage portion is that it can be placed even in bent portions of the handlebars to provide more space (it can be longer) than a storage portion of a firm material, which could be placed only in the straight portion at the end of the handlebars. On top of that, the compression storage portion dampens vibrations and thus the noise that could be generated while riding.

Preferably, the material used is abrasion resistant so there is no risk of grazing or tearing thereof by placement into the handlebars, and simultaneously, it is strong enough so there is no risk of rupture of the compression storage portion, even when bigger force is required for placing it inside the handlebars. Preferably, such a material is used that there is no significant friction between the compression storage portion and the inside of the handlebars.

The retraction element is used for retracting the compression storage portion into the handlebars. Therefore, preferably first the free end (i.e., the end not connected to the compression storage portion) passes (is dropped) through the handlebars and then it is pulled, thereby retracting the compression storage portion into the handlebars all the way to the other end thereof provided with the plug. The retraction element, e.g., a cord, should thus be longer than the handlebars such that the free end is accessible and can be pulled, and it should be firm enough so there is no risk of rupture thereof, even when bigger force is required for placing the compression storage portion inside the handlebars.

The compression storage portion can be fastened inside the handlebars thanks to its shape, i.e., by prestress between the compression storage portion and a wall of an opening in the handlebars. For example, prior to being placed in the handlebars, the compression storage portion can have a diameter larger than the opening in the handlebars, when the retraction element is pulled (i.e., due to the axial force), the compression storage portion is elongated and thus narrowed such that it can be easily retracted into the handlebars. After releasing the retraction element, the compression storage portion tends to expand, therefore, prestress is created between the compression storage portion and the inside of the handlebars, and the compression storage portion is fastened in the handlebars.

The plug, which can be a standard plug for the handlebars, in other words an end piece for the handlebars, is used to seal or close the entrance to the opening in the handlebars. Preferably, it helps to secure the first aid kit in the handlebars. For example, when the plug is (partially) inserted into the handlebars, a prestress can be created between the plug and the internal wall of the opening in the handlebars, and this prestress then holds the plug in place. The plug is adjustable so that it can be used to define a clearance in the handlebars. The same plug can then be used in several types of handlebars with various diameters of the openings in the handlebars.

The first aid kit into bicycle handlebars according to the invention then preferably comprises a firm storage portion which comprises a plug. The firm storage portion is insertable into the handlebars and defines additional space for storing objects, e.g., bandages, medicines, disinfectants, tweezer, etc. Said plug can be used to fix the firm storage portion in the handlebars. The firm storage portion can be placed in the handlebars from the side opposite to the compression storage portion after the compression storage portion is retracted into the handlebars such that the access to the retraction element is no longer needed.

The retraction element preferably comprises a lug attached to a free end of the retraction element. The lug can simply be a knot or a loop at the free end. Preferably, the lug is a small weight, for example a steel screw or a nut or a ball with a through opening (bead). The lug makes it easier to pass the free end through the handlebars and/or pull on the free end when retracting the compression storage portion.

The plug (i.e. one or both of the above mentioned) can comprise a flexible cylinder and a screw, wherein the flexible cylinder is adjustable to a first position and a second position, wherein in the first position, the external diameter of the flexible cylinder is smaller than the diameter of the opening in the handlebars, and in the second position, the flexible cylinder is axially pressed by the screw such that the diameter of the flexible cylinder is larger in the second position than in the first position. Therefore, for example, the flexible cylinder is provided with a through opening in the axis, into which a screw is inserted. By tightening the screw (e.g., in a nut with a diameter larger than the opening in the flexible cylinder such that the flexible cylinder is pressed between the screw and the nut), the flexible cylinder is compressed, and thus expanded radially. This defines a clearance between the plug and the opening in the handlebars and creates a prestress which fastens the plug (and, together with it, for example, one of the storage portions) in the opening in the handlebars. The flexible cylinder can be, for example, a cylinder or a hose of silicone or rubber. The plug can be e.g., a cylindrical, conical, or any other element of a flexible material which stays in place when pushed into the handlebars due to the prestress.

Preferably, the plug of the compression storage portion further comprises a portion with an external thread and a complementary portion with an internal thread, wherein the other end of the compression storage portion is fastened between the portion with an internal thread and the portion with an external thread. The other end of the compression storage portion (i.e., the end not connected to the retraction element) is therefore fastened between the portion with an internal thread and the portion with an external thread. Thanks to this, the other end of the compression storage portion can be not only fastened to the plug but also closed, provided that this other end is used to insert objects to the compression storage portion or taking them out.

Preferably, one portion from the portion with an internal thread and the portion with an external thread is provided with an opening with another internal thread complementary to the thread of the screw of the given plug, wherein the screw is fastened in the opening with another internal thread. The flexible cylinder is then pressed between the screw and the given portion. The individual portions of the plug are then connected with one another and with the compression storage portion by means of said threads.

Preferably, the firm storage portion comprises a first cylindrical wall and a second cylindrical wall (i.e., walls forming a portion of the cylinder shell), wherein the first and the second cylindrical walls are rotatable relative to each other around their common axis, wherein the first cylindrical wall is closed at one end by a bottom and at the other end, it is closed by a plug. Therefore, the first cylindrical wall is firmly closed at both ends (i.e., bases), and the second cylindrical wall is used to open and close the firm storage portion.

In a preferred embodiment of the first aid kit into bicycle handlebars of the present invention, the compression storage portion is made of mesh. The mesh material does not have to be flexible per se, but it is interwoven in such a manner that pulling in the longitudinal (axial) direction causes radial shrinkage and thus compression of the contents stored in the said mesh. On the other hand, pressing in the longitudinal direction can lead to partial unweaving of the mesh, thereby facilitating access to the contents of the compression storage portion.

An advantage of the mesh is a high strength and low adhesion to the metal wall of the opening in the handlebars (and hence low friction when placing the compression storage portion in the handlebars). Furthermore, the cross-section of the cylindrical portion of the mesh is significantly narrowed under tension in the axis such that retraction thereof into the handlebars is facilitated, especially if soft and/or flexible objects, such as a bandage material, are placed therein. The mesh can be a conventional plastic mesh, which is used in many applications as a protective and/or packaging material, e.g., for electrical installation material, or it can be, for example, a mesh of a metallic material, or a combination of plastic and metal.

DESCRIPTION OF THE DRAWINGS

A summary of the invention is further clarified using exemplary embodiments thereof, which are described with reference to the accompanying drawings, in which.

EXEMPLARY EMBODIMENTS OF THE INVENTION

Said embodiments show exemplary variants of the embodiments of the invention, which, however, have no limiting effect from the point of view of the scope of protection.

Figure 1:
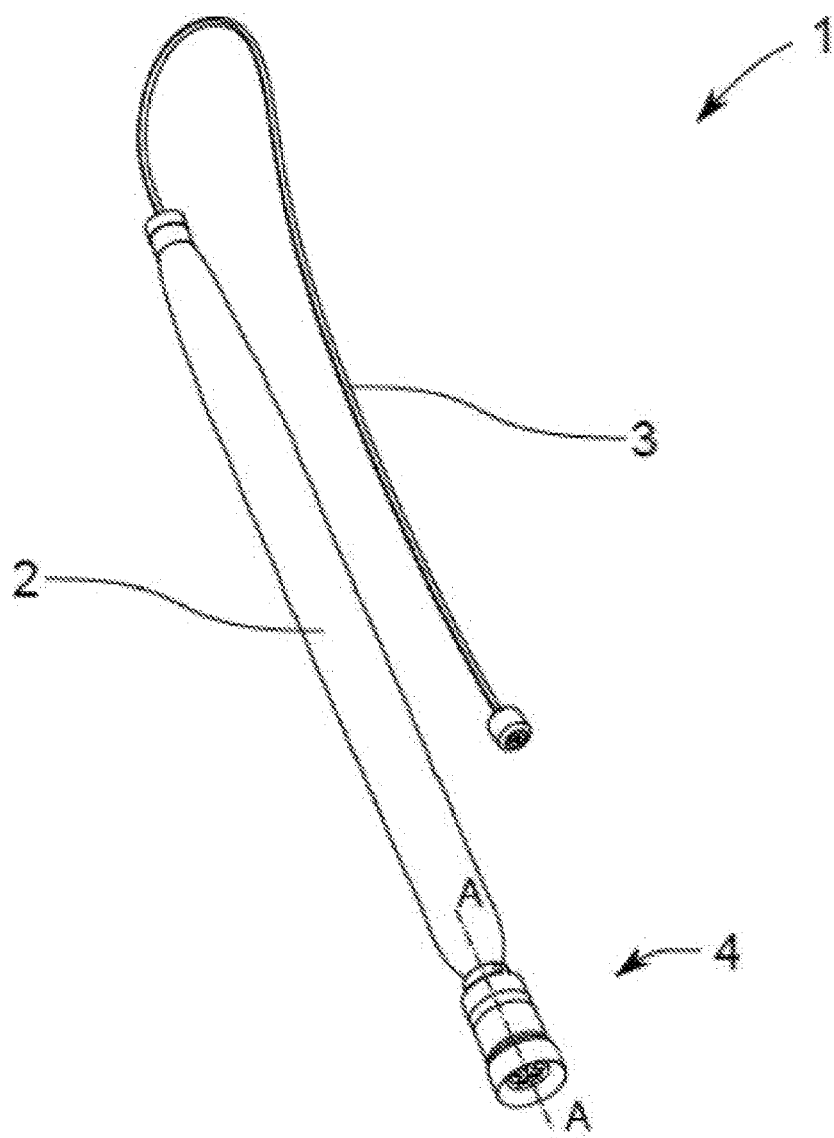
FIG. 1 shows a first aid kit into bicycle handlebars of the invention.
Figure 2:
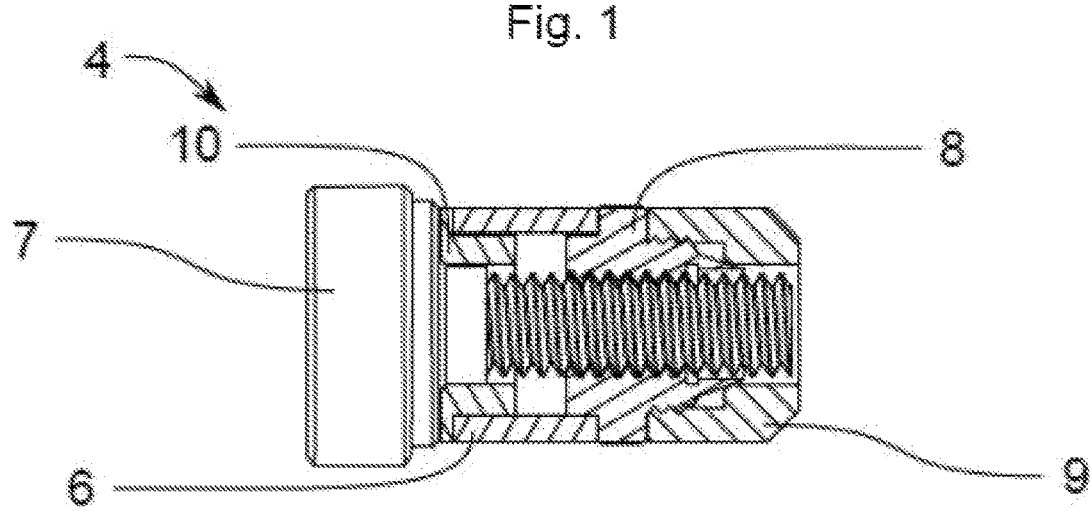
FIG. 2 shows A-A section of FIG. 1, made through a plug attached to a compression storage portion.
Figure 3:
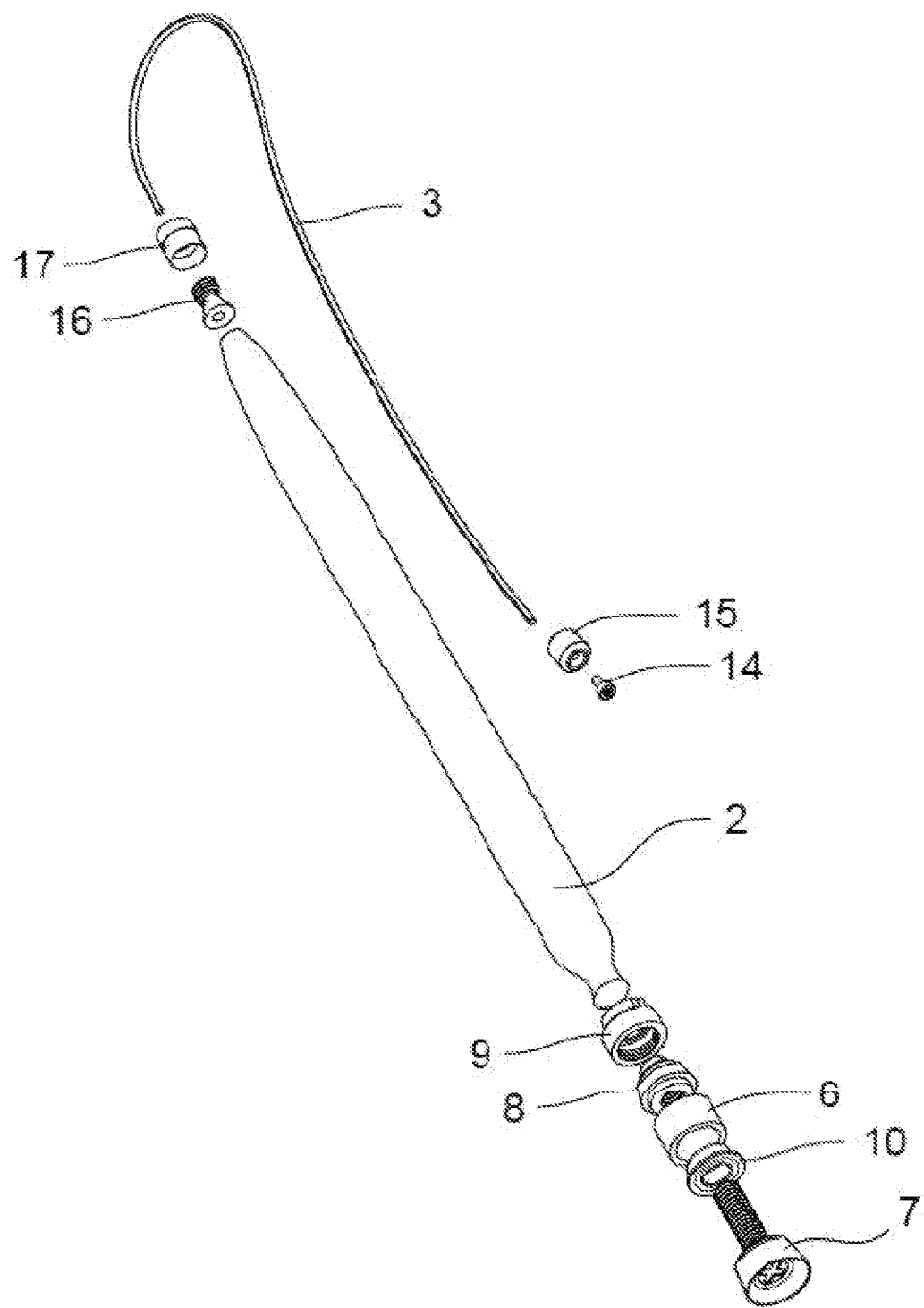
FIG. 3 shows an exploded view of the first aid kit into bicycle handlebars of FIG. 1.

The first aid kit 1 for the inside of bicycle handlebars shown in FIGS. 1 and 3 comprises a compression storage portion 2 made of mesh, for example polyethylene, a retraction element 3, and a first plug 4. Furthermore, the first aid kit 1 comprises a firm storage portion 5 comprising a first and a second cylindrical walls 11, 12, and a second plug 4. In this embodiment, the retraction element is a cord, but alternatively, another element can be used, e.g., a wire or a wire bundle, a fibre bundle, a chain, etc.

The compression storage portion 2 is used to store soft parts of the first aid kit, for example, several bandage rolls, rolled up patch, etc., can be stored therein. At the first end thereof, the compression storage portion 2 is fastened to the retraction element 3 by means of a screw 16 for fastening the retraction element and a nut 17 for fastening the retraction element, wherein the first end of the compression storage portion 2 is mounted on the retraction element fastening screw 16, and then the retraction element fastening nut 17 is screwed onto it such that the first end is firmly fastened between the given complementary threads. A through opening leads through the retraction element fastening screw 16, through which the retraction element 3 passes, the end of the retraction element 3 which is located inside the compression storage portion 2 is provided with a knot in order to firmly fasten the retraction element 3 in the given retraction element fastening screw 16, and therefore, to fasten it to the compression storage portion 2. The opposite free end of the retraction element 3 is similarly provided with a lug comprising a lug screw 14 and a lug nut 15, the lug being used to facilitate the passing of the retraction element 3 through the handlebars.

The first plug 4 comprises a screw 7, a flexible cylinder 6, which in this embodiment is a rubber hose, a washer 10, a portion 9 with an internal thread and a complementary portion 8 with an external thread. All these components have a cylindrical or approximately cylindrical shape and, when assembled, have a common axis. A through opening with another thread leads axially through the portion 8 with an external thread, into which the screw 7 can be threaded. In this embodiment, the washer 10 has a wider section and narrower section, wherein the narrower section has a diameter smaller than or equal to the internal diameter of the flexible cylinder 6 such that the flexible cylinder 6 can be mounted thereon, and the wider section has a diameter that is approximately equal to the external diameter of the flexible cylinder 6 and is used to separate the flexible cylinder 6 from the screw 7. The portion 8 with an external thread also has a wider and a narrower section, wherein the wider section is used as a bearing surface for the flexible cylinder 6 and for the portion 9 with an internal thread. The narrower section is chamfered in the direction away from the wider section for easier insertion into the mesh and comprises an external thread.

As shown in the exploded view of FIG. 3, the washer 10 and then the flexible cylinder 6 are mounted on the screw 7, and in turn, the portion 8 with an external thread (comprising an opening with another thread adapted particularly for engaging with the thread on the screw 7) is mounted and screwed onto the screw 7. By tightening the portion 8 with an external thread on the screw 7, the flexible cylinder 6 is pressed between the portion 8 with an external thread and the head of the screw 7. As a result of this pressing, the flexible cylinder 6 expands such that this flexible cylinder 6 is then convex. Therefore, by tightening the screw 7 with the portion 8 with an external thread, prestress is created between the flexible cylinder 6 and the handlebars at the first plug 4 inserted into the bicycle handlebars such that the first plug 4 is fixed in the handlebars despite any small clearance between the wall of the opening in the handlebars and the portion of the first plug 4 inserted into this opening. A detailed view of this first plug 4 is shown in a section in FIG. 3.

Alternatively, a flexible element in the shape of a truncated pyramid can be used to define the clearance and/or fasten the plug in the handlebars, which is simply pushed into the handlebars with the narrower end far enough to stay in place securely in the handlebars. Alternatively, instead of a flexible cylinder, the plug can have a flexible element that, when the plug is inserted into the handlebars, presses against the opening in the handlebars, for example, it can be a spring that is pressed when the plug is being inserted into the handlebars and subsequently exerts a force against the wall of the opening in the handlebars. A variety of plugs and end pieces is known in the art and is available on the market which can be used as a part of the present invention.

The portion 9 with an internal thread comprises a through opening in which the given internal thread is created. The other end of the compression storage portion 2 is inserted into this opening, and then the portion 8 with an external thread is screwed into it by means of the external thread thereof such that the mesh comprising the compression storage portion 2 is firmly fastened in this thread. The head of the screw 7 has a larger diameter than the opening in the handlebars into which the first aid kit 1 is to be inserted such that the head of the screw 7 always projects from the handlebars and it is possible to hold it and use it to pull the first aid kit 1 out of the handlebars. For firmer holding, the head of the screw 7 is provided with anti-slip elements, grooves in this embodiment, created on the cylindrical surface of the head of this screw 7, alternatively, projections or cover with an anti-slip material, a metal ring for a finger, or a combination of said anti-slip elements.

Figure 4:
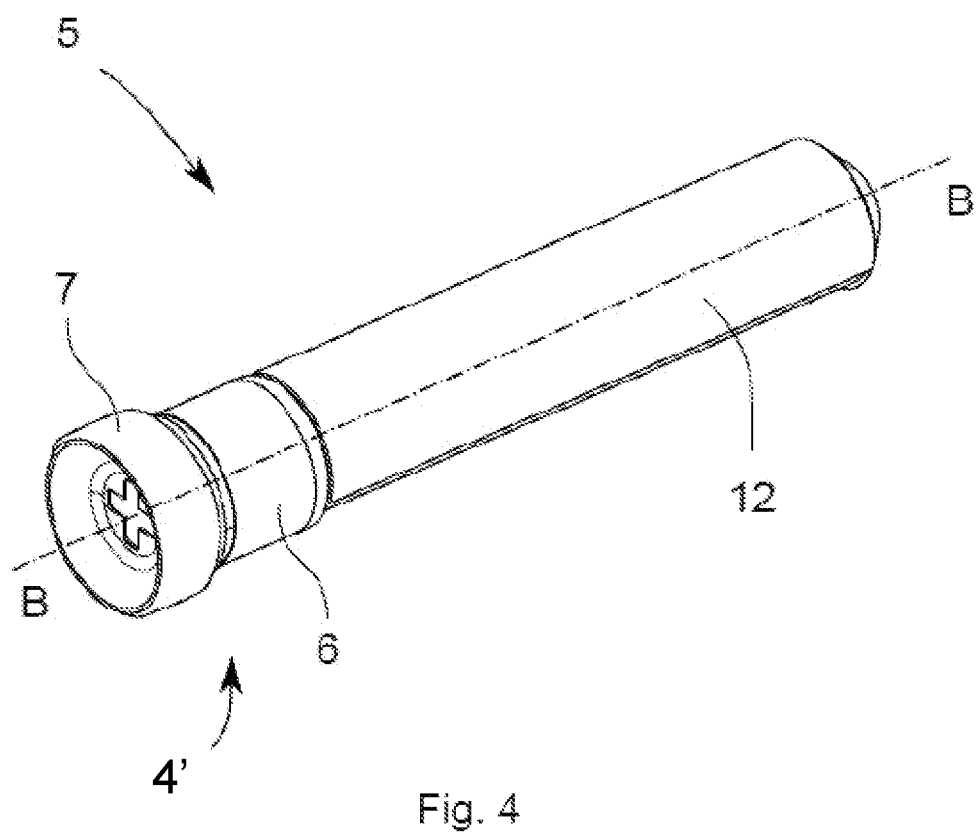
FIG. 4 shows a firm storage portion of the first aid kit of the invention.
Figure 5:
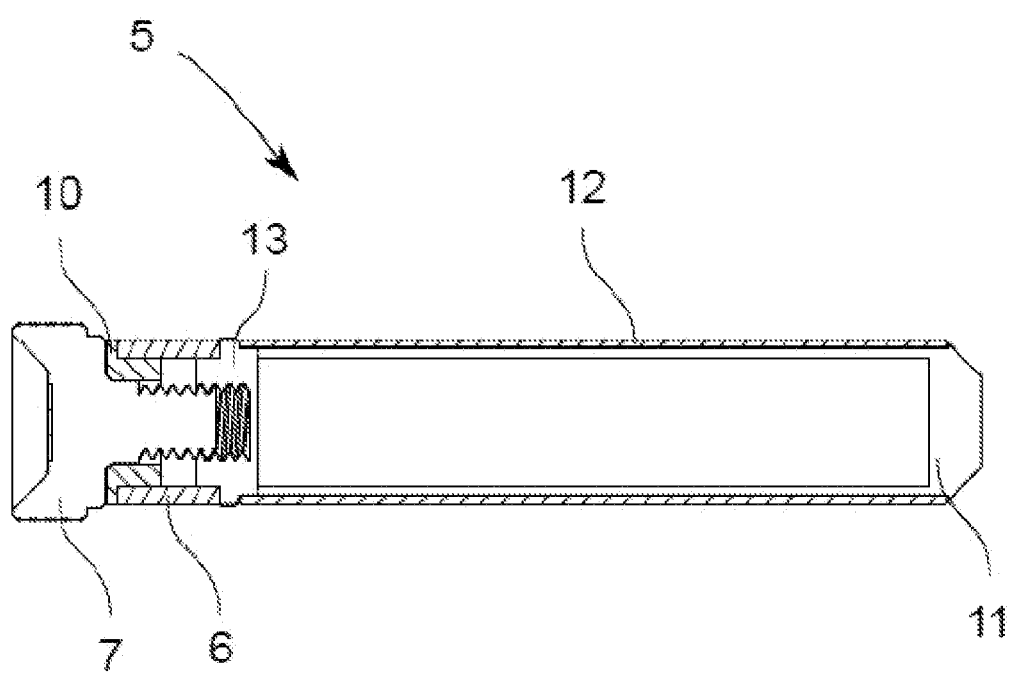
FIG. 5 shows B-B section of FIG. 4 is shown, made through the plug which is a part of the firm storage portion.
Figure 6:
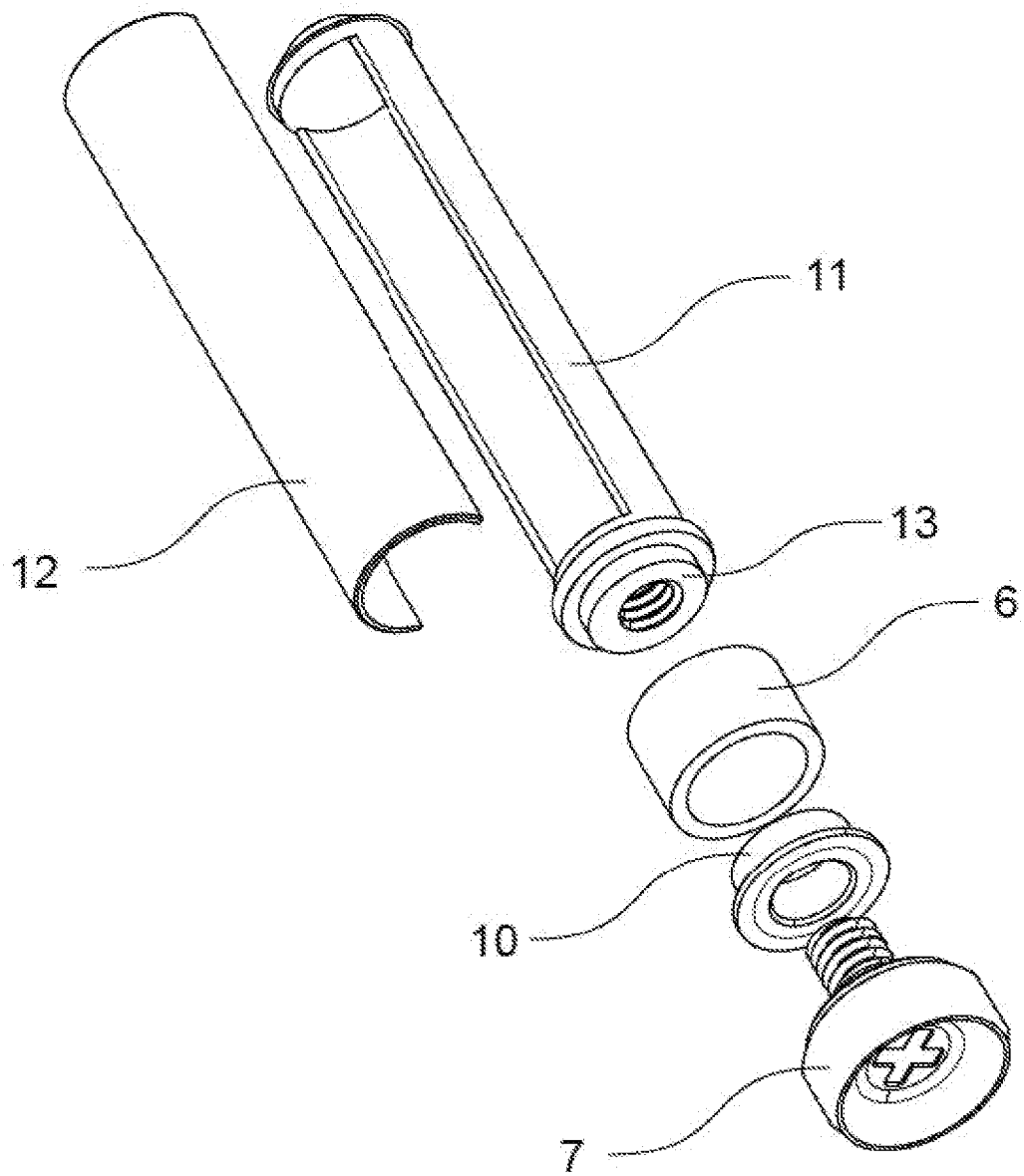
FIG. 6 shows an exploded view of the firm storage portion of the first aid kit into bicycle handlebars of the invention.

The firm storage portion 5 comprises a first and a second cylindrical walls 11, 12, and a second plug 4, as mentioned above and shown in FIGS. 4 and 6. The first cylindrical wall 11 is portion of about 220° of the cylindrical surface, at one end (i.e., at one base of the given cylinder), this wall is provided with a circular bottom, at the other end, it is firmly connected to the second plug 4. The second cylindrical wall 12 is portion of about 180° of the cylindrical surface and is opened in the direction towards both bases. The second cylindrical wall 12 has a larger diameter than the first cylindrical wall 11 and is mounted thereon. Both cylindrical walls can be rotated relative to each other such that the second cylindrical wall 12 functions as a door for the given opening of about 140° in the first cylindrical wall 11. In this embodiment, the first and the second cylindrical walls 11, 12 are connected to each other using a rubber band (not shown) which is put thereon and presses them together. The axial movement between the cylindrical walls is then prevented by overlaps on the circular bottom and on the second plug 4. Thus, inside the firm storage portion 5, a closable cylindrical space is defined, suitable e.g., for medications, safety pins, needles, disinfectant bottle, etc.

The second plug 4, comprises a second screw 7, a second washer 10, a second flexible cylinder 6, and a nut 13. The embodiment of these parts is similar to the first plug 4 described above, wherein the nut 13 substitutes the portion 8 with an external thread and is used to screw onto the second screw 7. In contrast with the portion 8 with an external thread, the nut 13 does not comprise an external thread, instead, it is firmly connected to the first cylindrical wall 11. By tightening the nut 13 on the second screw 7, i.e., by bringing them closer together, the second flexible cylinder 6 is pressed between them, thereby making it possible again to define a possible clearance between the handlebars and the second plug 4. The head of the second screw 7 is again wider than the opening in the handlebars such that it projects from the handlebars and it is possible to use it to pull the firm storage portion 5 out of the handlebars.

The firm storage portion 5 comprises a first and a second cylindrical walls 11, 12, and a second plug 4, as mentioned above and shown in FIGS. 4 and 6. The first cylindrical wall 11 is portion of about 220° of the cylindrical surface, at one end (i.e., at one base of the given cylinder), this wall is provided with a circular bottom, at the other end, it is firmly connected to the second plug 4. The second cylindrical wall 12 is portion of about 180° of the cylindrical surface and is opened in the direction towards both bases. The second cylindrical wall 12 has a larger diameter than the first cylindrical wall 11 and is mounted thereon. Both cylindrical walls can be rotated relative to each other such that the second cylindrical wall 12 functions as a door for the given opening of about 140° in the first cylindrical wall 11. In this embodiment, the first and the second cylindrical walls 11, 12 are connected to each other using a rubber band (not shown) which is put thereon and presses them together. The axial movement between the cylindrical walls is then prevented by overlaps on the circular bottom and on the second plug 4. Thus, inside the firm storage portion 5, a closable cylindrical space is defined, suitable e.g., for medications, safety pins, needles, disinfectant bottle, etc.

After the compression storage portion 2 is retracted into the handlebars, the retraction element 3 can be placed freely into the handlebars between both storage portions. In some alternative embodiments, after passing the retraction element 3 through and pulling the compression storage portion 2 into the handlebars, it is possible to store the lug screw 14 with the lug nut 15 in the firm storage portion 5 at the free end of the retraction element 3 such that this screw with the nut cannot move freely in the handlebars and make noise. For this purpose, an aperture extending to the opening in the first cylindrical wall 11 can be provided in the bottom of the firm storage portion 5 such that after the screw with the nut attached to the retraction element 3 is placed in the open firm storage portion, the retraction element 3 can fit in this aperture and the firm storage portion 5 can then be easily closed. Alternatively, a space for the retraction element 3 can be located between the first and the second cylindrical walls 11, 12, instead of said zo aperture in the bottom such that the retraction element 3 does not prevent closing of the firm storage portion 5.

Alternatively, the firm storage portion 5 can be designed in any other way. For example, it can be a housing formed by a cylindrical wall with one base and at another base provided with elements for fastening the plug 4, which is then used as a lid for this housing. The plug 4 can be fastened by, for example, a thread, using complementary projections and recesses which fit into each other and prevent unintentional movement of the plug 4 relative to the firm storage portion, etc.

In addition to objects related to the first aid kit, storage portions of the invention, or one of them, can store anything else, e.g., money, tools, spare flashlight batteries, etc.

The first aid kit 1 of the present invention can comprise a plurality of compression storage portions 2 placed in a sequence and connected at their ends by e.g., a plastic coupling with threads at both ends, into which the mesh is fastened as described for plugs 4 above.

LIST OF REFERENCE NUMERALS

1—First aid kit
2—Compression storage portion
3—Retraction element
4—Plug
5—Firm storage portion
6—Flexible cylinder
7—Screw
8—Portion with an external thread
9—Portion with an internal thread
10—Washer
11—First cylindrical wall
12—Second cylindrical wall
13—Nut
14—Lug screw
15—Lug nut
16—Retraction element fastening screw
17—Retraction element fastening nut

The invention claimed is:

1. A first aid kit for use in inside bicycle handlebars comprising a compression storage portion, wherein the compression storage portion defines a space adapted for storing objects and, furthermore, the first aid kit comprises an elongated retraction element attached to a first end of the compression storage portion, wherein a second end of the compression storage portion is provided with a plug and wherein the retraction element is configured for pulling the compression storage portion into the handlebars.

2. The first aid kit for the inside of bicycle handlebars of claim 1, further comprising a firm storage portion, wherein the firm storage portion comprises a plug.

3. The first aid kit for the inside of bicycle handlebars of claim 2, wherein the firm storage portion comprises a first cylindrical wall and a second cylindrical wall, wherein the first and the second cylindrical walls are rotatable relative to each other around a common axis, wherein the first cylindrical wall is closed at one end by a bottom and at another end by the plug.

4. The first aid kit for the inside of bicycle handlebars of claim 1, wherein the retraction element comprises a lug attached to a free end of the retraction element.

* * * * *